United States Patent [19]

Schmidt et al.

[11] Patent Number: 4,628,109

[45] Date of Patent: Dec. 9, 1986

[54] 2-KETOSULFONAMIDES AND PROCESS FOR THEIR PREPARATION

[75] Inventors: Erwin Schmidt; Dieter Günther, both of Kelkheim; Klaus-Dieter Kampe, Bad Sodem am Taunus, all of Fed. Rep. of Germany

[73] Assignee: Hoechst Aktiengesellschaft, Frankfurt, Fed. Rep. of Germany

[21] Appl. No.: 624,938

[22] Filed: Jun. 27, 1984

[30] Foreign Application Priority Data

Jun. 30, 1983 [DE] Fed. Rep. of Germany ....... 3323510

[51] Int. Cl.⁴ .................. C07C 143/74; C07C 143/78
[52] U.S. Cl. ......................... 560/13; 560/12; 560/150; 564/87; 564/88; 564/95
[58] Field of Search ............... 564/95, 88, 87; 560/13, 560/150, 12

[56] References Cited

U.S. PATENT DOCUMENTS 4,448,988  5/1984  Gunther ............................ 564/95

FOREIGN PATENT DOCUMENTS 0001051  2/1981  European Pat. Off. .

Primary Examiner—Michael L. Shippen
Attorney, Agent, or Firm—Curtis, Morris & Safford

[57] ABSTRACT

The invention relates to new 2-ketosulfonamides of the formula

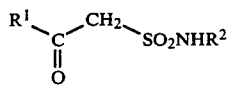

and to a process for their preparation, wherein the 3-amino-2-sulfamoylalk-2-enoic acid esters of the formula

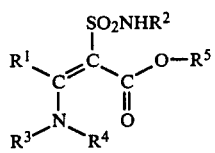

obtained by reacting 3-aminoalk-2-enoic acid esters of the formula

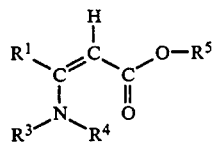

with amidosulfonyl chlorides of the formula $X\text{-}SO_2\text{-}NH\text{-}R^2$, are subjected to hydrolysis and decarboxylation. The invention also relates to the 3-amino-2-sulfamoylalk-2-enoic acid esters which can be isolated as intermediates.

4 Claims, No Drawings

2-KETOSULFONAMIDES AND PROCESS FOR THEIR PREPARATION

2-Ketosulfonamides are valuable intermediates. They are used as starting materials for pigments (cf. German Offenlegungsschrift No. 3,116,129) or chemotherapeutics (cf. Chem. Pharm. Bull. 21 (1973), 5, 1080–1089). Hitherto, it has only been possible to prepare acetonesulfonamide by oxidizing 2-hydroxypropanesulfonamide (cf. German Offenlegungsschrift No. 3,116,129). However, this precursor is only obtainable via the unstable 2-hydroxypropanesulfonyl chloride, which is difficult to prepare. Nitrogen-substituted acetonesulfonamides, on the other hand, cannot be prepared by this method, showing the narrow limitation of the said process.

In a second process for the preparation of 2-ketosulfonamides, which is particularly suitable for the preparation of aromatic 2-ketosulfonamides, an appropriate acetophenone is used as the starting material.

This is converted to the corresponding sulfonic acid with sulfur trioxide. After reaction with phosphorus chlorides (for example phosphorus trichloride or phosphorus pentachloride) to give the sulfonyl chloride, the latter is reacted with amines to give the sulfonamide (cf. J. Amer. Chem. Soc. 75, 2525 (1953)).

However, the use of such reactive compounds as sulfur trioxide or phosphorus chlorides leads to side reactions necessitating costly purification of the intermediates.

As a result of the shortcomings of both processes for the preparation of 2-ketosulfonamides, the object was to find a simpler, more widely applicable method for the preparation of these compounds.

A process has now been found which makes it possible to prepare nitrogen-substituted 2-ketosulfonamides in a simple manner by reacting certain 3-aminoalk-2-enoic acid esters with halogenosulfonamides in the presence of a base, and saponifying and decarboxylating the resulting reaction product.

The invention thus relates to the process defined in the claims, to the intermediates produced during this process and to the substituted 2-ketosulfonamides prepared by this process.

The 2-ketosulfonamides prepared according to the invention are compounds of the formula I

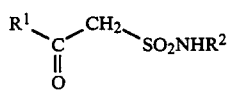

in which
$R^1$ denotes a $C_1$–$C_{11}$ alkyl radical, a phenyl radical optionally substituted by halogen atoms or $C_1$–$C_4$ alkoxy, nitro or $C_1$–$C_2$ alkoxycarbonyl groups, the number of substituents on the phenyl radical being at most three, or a phenyl-$C_1$–$C_2$-alkyl radical in which the phenyl group can be substituted by one or two halogen atoms or $C_1$–$C_2$ alkoxy groups, and
$R^2$ denotes a hydrogen atom, a $C_1$–$C_{12}$ alkyl radical or a $C_6$–$C_{12}$ aryl radical which can be substituted by groups containing 0 to 3 heteroatoms and 0 to 2 carbon atoms.

The protection does not include the compounds of the formula (I) in which $R^1$ is a $C_1$–$C_4$ alkyl or phenyl radical and $R^2$ denotes hydrogen, and
$R^1$ is a phenyl radical and $R^2$ denotes a phenyl, cyclohexyl or n-butyl radical.

The starting materials for the process according to the invention are 3-aminoalk-2-enoic acid esters of the formula II

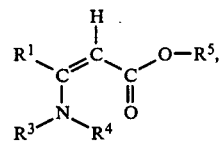

in which $R^1$ has the meaning given above, $R^3$ and $R^4$ are identical or different and denote hydrogen, $C_1$–$C_4$ alkyl radicals which can also be linked together to form a ring, or $C_6$–$C_{12}$ aralkyl or $C_6$–$C_{12}$ aryl radicals having 0 to 2 heteroatoms, and $R^5$ denotes a branched or unbranched $C_1$–$C_{18}$ alkyl radical, preferably a $C_1$–$C_4$ alkyl radical, which can contain heteroatoms, for example a 2-methoxyethyl or 2-chloroethyl radical. These compounds can exist in E and Z configurations in respect of the C=C double bond.

Examples of suitable aminoalk-2-enoic acid esters are 3-methylamino-, dimethylamino-, ethylamino-, diethylamino-, hydroxyethylamino-, i-propylamino-, butylamino-, dibutylamino-, pyrrolidino-, piperidino-, benzylamino-, phenylamino-, diphenylamino-, biphenylamino-, 2-, 3- or 4-chlorophenylamino- and 2-, 3- or 4-methoxyphenylaminoalk-2-enoic acid esters.

It is particularly preferred to use 3-aminocrotonic acid esters as starting materials for the process according to the invention.

The best yields are obtained with 3-aminocrotonic acid esters which still carry at least 1 hydrogen atom on the nitrogen atom.

To obtain reaction products which crystallize well, it is advantageous to use as starting materials 3-aminocrotonic acids esters which themselves already crystallize well. 3-Aminocrotonic and 3-anilinocrotonic acid esters, for example, are particularly suitable.

The 3-aminoalk-2-enoic acid esters of the formula (II) are reacted with an amidosulfonyl halide of the formula (III)

$$X\text{-}SO_2NH\text{-}R^2 \qquad \text{(III),}$$

in which $R^2$ has the abovementioned meaning and X denotes chlorine, bromine or fluorine, preferably chlorine.

According to the choice of the substituent $R^2$ in the amidosulfonyl halide, the process according to the invention makes it possible to prepare a large number of 2-ketosulfonamides variously substituted on the nitrogen. Examples of suitable starting materials are methylamido-, ethylamido-, 1-propylamido-, tert.-butylamido-, n-butylamido-, hexylamido-, phenylamido-, 2-chlorophenylamido-, 3-methoxyphenylamido-, 4-methylphenylamido-, diphenylamido-, 2,4-diethoxyphenylamido-, 3,4,5-triethoxyphenylamido- and 4-nitrophenylamido-sulfonyl chlorides.

Particular preference is given to amidosulfonyl chloride unsubstituted on the nitrogen, which is particularly easy to obtain from chlorosulfonyl isocyanate [R. Graf, Angew. Chem. 80, 180 (1968)].

In the reaction of the 3-aminoalk-2-enoic acid esters with the amidosulfonyl halide, it is necessary to add at least one equivalent of a base which binds the hydrogen halide liberated. An excess of 3-aminoalk-2-enoic acid ester can be used for this purpose. It is more advantageous to use an auxiliary base which is inexpensive or can easily be regenerated. Particularly suitable auxiliary bases are all tertiary or sterically hindered amines, for example trimethylamine, triethylamine, triethylenediamine (DABCO), pyridine, dimethylamine, dicyclohexylamine, triphenylamine and N-methylpiperidine.

However, the reaction can also be carried out in the presence of inorganic bases of the alkali or alkaline earth metals, such as lithium hydroxide, sodium hydroxide, sodium carbonate, sodium bicarbonate, potassium hydroxide, potassium carbonate, potassium bicarbonate, calcium hydroxide or magnesium hydroxide, as the solid, in solution or under phase transfer conditions.

The reactants are added in any order, simultaneously or successively. It is advantageous to introduce the particularly reactive amidosulfonyl chloride first and to add the base and the 3-aminoalk-2-enoic acid ester simultaneously, either separately or as a mixture. It is advantageous to use approximately equimolar quantities of the components, there being no advantage in using excesses of reactants. The components are advantageously brought together in the temperature range between $-10$ and $+40°$ C. The reaction proceeds very slowly below this range and the yield gradually decreases above it.

The reaction can be carried out in the presence or absence of inert solvents or diluents, individually or as mixtures. Examples of suitable solvents are: hydrocarbons such as pentane, hexane, light petroleum ether, ligroin, benzene, toluene and xylene; chlorohydrocarbons such as methylene chloride, tetrachloroethylene, carbon tetrachloride, chloroform, chloropentane, chlorobenzene and dichlorobenzene; ethers such as dimethyl ether, diethyl ether, di-i-propyl ether, phenyl ethyl ether, dioxane, tetrahydrofuran and dimethoxyethane; and carboxylic acid derivatives such as ethyl acetate, acetonitrile and dimethylformamide. Examples of other suitable solvents are phosphoric acid tris-dimethylamide or liquid sulfur dioxide, if appropriate under pressure.

The requisite reaction time depends on the reactivity of the components and the reaction temperature. It must be determined from case to case. It is advantageously limited to 2–24 hours by choosing the reaction conditions.

The reaction yields 3-amino-2-sulfamoylalk-2-enoic acid esters of the formula (IV)

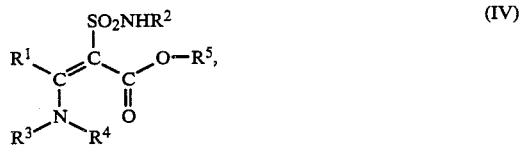

in which $R^1$, $R^2$, $R^3$, $R^4$ and $R^5$ have the abovementioned meanings.

The preferred 3-amino-2-sulfamoylalk-2-enoic acid esters of the formula (IV) are those in which $R^1$ denotes a $C_1$–$C_4$ alkyl radical, a phenyl radical, a phenyl radical substituted by one or two chlorine atoms or a benzyl radical, $R^2$ denotes a hydrogen atom, a straight-chain $C_1$–$C_4$ alkyl radical or a phenyl radical, $R^3$ denotes a hydrogen atom, a methyl group or a phenyl radical, $R^4$ denotes a hydrogen atom and $R^5$ denotes a $C_1$–$C_4$ alkyl radical.

The intermediates of the formula (IV) are saponified under acidic or alkaline conditions and decarboxylated. This is carried out using the conditions known in the literature for the saponification of enamines and esters and for the decarboxylation of acetoacetic acid derivatives. For example, it is possible first to saponify the ester group in an alkaline medium and then decarboxylate under acidic conditions and saponify the enamine group. This procedure can also be carried out in the reverse order. It is further possible to carry out the saponification of the ester and enamine groups and the decarboxylation in one step under acidic conditions.

It is also possible to cleave the ester group in dimethyl sulfoxide, in the presence of alkali metal halides, at elevated temperature.

At least stoichiometric quantities of water are required for the saponification. Acids and bases can be added in concentrated or dilute solution or without a solvent. The reaction is advantageously carried out in aqueous media. Solvents or diluents, such as methanol, ethanol, acetone, methylene chloride, benzene, toluene and chlorobenzene, can be added to the reaction mixture.

The saponification and decarboxylation can be carried out in a wide range of temperatures. The cleavage of the ester group in DMSO is generally carried out at $100°$–$180°$ C.; the saponification of the enamine and ester proceeds relatively rapidly at temperatures as low as about $0°$ C. At $80°$–$120°$ C., the cleavage and saponification of the tert.-butyl ester is complete in 1–2 hours.

In the acid hydrolysis of the 3-amino-2-sulfamoylalk-2-enoic acid esters, 2-sulfamoyl-3-ketoalkanoic acid esters of the formula (V)

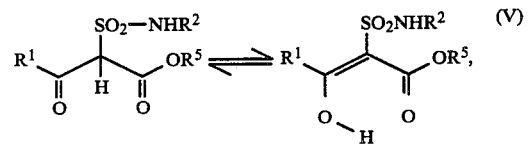

in which $R^1$, $R^2$ and $R^5$ have the abovementioned meanings, can be isolated as intermediates.

As shown in the structural formula, these compounds can exist in two tautomeric forms, as is known for $\beta$-ketocarboxylic acid esters.

Preferred 2-sulfamoyl-3-ketoalkanoic acid esters of the formula (V) are those in which $R^1$ denotes a $C_1$–$C_4$ alkyl group, a phenyl radical, a phenyl radical substituted by one or two chlorine atoms or a benzyl radical, $R^2$ denotes a hydrogen atom and $R^5$ denotes a $C_1$–$C_4$ alkyl radical.

The preferred compounds of the formulae (IV) and (V) are distinguished, inter alia, by a particularly good accessibility on account of the better yields and tendency to crystallize.

It is particularly advantageous to use tert.-butyl 3-aminocrotonates. They can be particularly easily saponified in one step to the 2-ketosulfonamide and decarboxylated with cleavage of $CO_2$ and i-butene.

The 2-ketosulfonamides of the formula (I) according to the invention are precursors for new plant-protection agents and pharmaceuticals. However, they are analogs of the acylacetamides, which in turn are very important as coupling components for azo dyes and pigments.

The examples which follow are intended to illustrate the invention.

EXAMPLE 1

Tert.-butyl 2-amidosulfonyl-3-aminocrotonate

A mixture of 785 g (5 mol) of tert.-butyl 3-aminocrotonate, 510 g (5.05 mol) of triethylamine and 500 ml of acetonitrile was added dropwise, at 0° to 5° C., to a solution of 578 g (5 mol) of amidosulfonyl chloride in 2500 ml of acetonitrile (dried over a molecular sieve).

After stirring for 2 hours at the same temperature and for a further 6 hours at room temperature, 835 ml of 6N sodium hydroxide solution were added while cooling with ice, the mixture was stirred for one hour and the aqueous layer was separated off and extracted a further twice with acetonitrile. After evaporation of the acetonitrile solution in a rotary evaporator, a residue was obtained which was recrystallized from methanol/water.

Yield: 1004 g=85% (of theory).
Melting point: 134°–135° C. (decomposition).

The same result was obtained when using the equivalent quantity of tert.-butyl 3-aminocrotonate, dimethylaniline or pyridine in place of triethylamine.

Acetonesulfonamide 236 g (1 mol) of tert.-butyl 2-amidosulfonyl-3-aminocrotonate were boiled under reflux in 1000 ml of 2N hydrochloric acid until all the solid had dissolved and the evolution of gas had ceased (about 2 hours).

After evaporation, the residue was extracted with acetonitrile and the resulting solution was evaporated again in the rotary evaporator. The crystallizing residue (140 g) was recrystallized from i-propanol. This yielded 122 g (89% of theory) of acetonesulfonamide of melting point 74°–76° C. (i-propanol).

EXAMPLE 2

Ethyl 2-amidosulfonyl-3-aminocrotonate

A solution of 26 g (0.2 mol) of ethyl 3-aminocrotonate in 70 ml of absolute acetonitrile was rapidly added dropwise, at −2° C.–0° C., to 50 ml of a 2 molar solution of amidosulfonyl chloride in anhydrous acetonitrile. The mixture was stirred for 45 minutes while cooling with ice, for 30 minutes until room temperature was reached and for 1 hour at room temperature, and cooled to about 1° C., and 16.5 ml of 6N NaOH were added dropwise at 1° C.–3° C. The resulting mixture was concentrated in vacuo at a bath temperature of 35° C. to a residual weight of 50 to 55 g, the residue was treated with 30 ml of water and the mixture was extracted several times with ethyl acetate. The combined extracts were dried with $Na_2SO_4$ and filtered and the filtrate was evaporated in vacuo. The remaining residue (32–35 g) was mixed thoroughly with about 100 ml of diisopropyl ether. The diisopropyl ether extract was poured off from the viscous, oily, partially crystalline mass. This was dissolved in 120 ml of boiling ethyl acetate. The hot solution was filtered with a filter aid. The product crystallized out of the filtrate on cooling (ice-bath). After the crystalline portion had been filtered off with suction and rinsed (with AcOEt), a further quantity of pure product could be obtained by concentrating the mother liquor. 15.6 g (75%) of ethyl 2-amidosulfonyl-3-aminocrotonate were thus obtained.

Melting point: 103°–104° C.

It was also possible to use 1,2-dimethoxyethane (glyme) as the solvent in place of acetonitrile.

The following were obtained by the same procedure as described above: ethyl 2-amidosulfonyl-3-methylaminocrotonate, melting point: 69°–70° C. (from ethyl acetate diisopropyl ether), yield: about 70%; and methyl α-amidosulfonyl-β-aminocinnamate, melting point: 141°–142° C. (from $CH_2Cl_2$), yield: about 70%; in this case, a relatively large quantity of $CH_2Cl_2$ was used as the organic extraction agent, from which the amidosulfonyl compound was immediately obtained pure by concentration. It was also possible to use ethyl acetate as the extraction agent.

Acetonesulfonamide 20.8 g of ethyl 2-amidosulfonyl-3-aminocrotonate were stirred with 200 ml of 2N sodium hydroxide solution for 18 hours at room temperature. The pH was adjusted to 1 with concentrated hydrochloric acid, a further 0.2 mol of concentrated hydrochloric acid was added and the mixture was boiled under reflux until the evolution of gas had ceased. After evaporation of the solution, the dry residue was extracted with acetonitrile. After renewed evaporation, the extract yielded 5.4 g (39% of theory) of acetone-N-sulfonamide.

Melting point: 74°–76° (i-propanol).

EXAMPLE 3

Tert.-butyl 2-N-methylamidosulfonyl-3-aminocrotonate 157 g (1 mol) of tert.-butyl 3-aminocrotonate and 105 g (1.04 mol) of triethylamine in 100 ml of methylene chloride were added dropwise, at 0° to 5° C., to a solution of 129.5 g (1 mol) of N-methylamidosulfonyl chloride in 500 ml of methylene chloride. After the reaction mixture had been left to stand overnight at room temperature, it was extracted three times by shaking with water, the organic solution was evaporated, the crystallizing residue was triturated with i-propyl ether and the mixture was filtered with suction.

Yield: 200 g (80% of theory).
Melting point: 102° C. (methanol/water).

Acetone-N-methylsulfonamide

The reaction product was boiled under reflux with 800 ml of 2N hydrochloric acid until all the solid had dissolved and the evolution of gas had ceased (about 2 hours). After evaporation in a rotary evaporator, the residue was extracted with acetonitrile and the extract was evaporated again. This yielded 115 g (95% of theory) of acetone-N-methylsulfonamide.

Melting point: 42° C. (methanol/$H_2O$).

EXAMPLE 4

Tert.-butyl 2-N-ethylamidosulfonyl-3-anilinocrotonate

A solution of 233.6 g (1 mol) of tert.-butyl 3-anilinocrotonate and 101 g (1 mol) of triethylamine in 200 ml of methylene chloride was added dropwise, at 0°–5° C., to a solution of 143.5 g (1 mol) of N-ethylamidosulfonyl chloride in 500 ml of methylene chloride. The mixture was stirred for 1 hour at the same temperature and for a further 6 hours at room temperature and extracted twice by shaking with water, and the methylene chloride solution was evaporated. This yielded 310 g (91% of theory) of tert.-butyl 2-N-ethylamidosulfonyl-3-anilinocrotonate.

Melting point: 65° C. (methanol).

Acetone-N-ethylsulfonamide

The reaction product was boiled under reflux with 500 ml of 2N hydrochloric acid for about 2 hours. After the evolution of gas had ceased, the pH was adjusted to 11 with 33% sodium hydroxide solution and the mixture was extracted with i-propyl ether. The aqueous solution was acidified again with hydrochloric acid and evaporated in vacuo. Extraction with acetonitrile and evaporation of the extract yielded 138 g (92% of theory) of acetone-N-ethylsulfonamide.

Melting point: 57° C. (i-propanol).

EXAMPLE 5

Tert.-butyl 2-N-phenylamidosulfonyl-3-anilinocrotonate

A solution of 46.6 g (0.2 mol) of tert.-butyl 3-anilinocrotonate and 21.0 g (0.21 mol) of triethylamine in 100 ml of methylene chloride was added dropwise, at 0°–5° C., to a solution of 38 g (0.2 mol) of phenylamidosulfonyl chloride in 200 ml of methylene chloride. The mixture was kept at 5° C. for 1 hour and left to stand overnight at room temperature. The methylene chloride solution was evaporated after extraction by shaking with water. This yielded 72.4 g (93% of theory) of a crystalline residue.

Melting point: 108° C. (methanol).

Acetone-N-phenylsulfonamide 19.4 g (50 mmol) of reaction product were boiled under reflux with 50 ml of 2N hydrochloric acid and 30 ml of ethanol until the evolution of gas had ceased (1 hour). 5 g of acetone-N-phenylsulfonamide crystallized out after cooling. Concentration of the mother liquor yielded a further 4 g.

Total yield: 84% of theory.

Melting point: 92° C. (methanol).

EXAMPLE 6

A solution of 22.7 g (0.1 mol) of tert.-butyl 3-morpholinocrotonate and 11 g (0.11 mol) of triethylamine in 20 ml of methylene chloride was added dropwise, at 30° C., to a solution of 16 g (0.1 mol) of phenylamidosulfonyl chloride in 50 ml of methylene chloride. After 6 hours, the mixture was extracted by shaking with water, the methylene chloride was distilled off and the residue was boiled with 100 ml of 2N hydrochloric acid until the evolution of gas had ceased. Acetone-N-phenylsulfonamide was separated from the reaction mixture chromatographically on silica gel with a mixture of 75% by volume of hexane and 25% by volume of ethyl acetate.

EXAMPLE 7

Ethyl 2-amidosulfonyl-3-aminohex-2-enoate

A solution of 10.72 g (68.2 mmol) of ethyl 3-aminohex-2-enoate in 20 ml of anhydrous acetonitrile was added dropwise, in about 15 minutes, at −5° C., to a solution of 4.10 g (35.5 mmol) of amidosulfonyl chloride in 20 ml of anhydrous acetonitrile. The mixture was stirred for 45 minutes at 0°–2° C., for 45 minutes at 1° C. to room temperature and for 1.5 hours at room temperature, 6.4 ml of 6N NaOH were added dropwise at about 4° C. and the reaction mixture was evaporated at a bath temperature of 38° C. to a residual weight of about 20 g. This residue was taken up in a mixture of 7 ml of water and about 100 ml of $CH_2Cl_2$, the phases were separated after thorough mixing and the aqueous phase was extracted several times more by shaking with $CH_2Cl_2$. The combined extracts were dried with $Na_2SO_4$ and filtered and the filtrate was evaporated in vacuo. The remaining residue was dissolved in ethyl acetate. Crystallization took place when diisopropyl ether was added. The crystalline mass was filtered off with suction, washed with diisopropyl ether and dried in vacuo. This yielded 7.60 g of pure ethyl 2-amidosulfonyl-3-aminohex-2-enoate of melting point 102°–103° C. (TLC-pure), = a yield of 90.6%.

2-Oxopentane-1-sulfonamide 2.36 g (10 mmol) of ethyl 2-amidosulfonyl-3-aminohex-2-enoate were dissolved in 15 ml of 2N sodium hydroxide solution at room temperature. After 16 hours, oily by-products were extracted with methylene chloride and the aqueous solution was acidified with excess concentrated hydrochloric acid and heated for 15 minutes to 90° C. After the evolution of gas had ceased, the mixture was evaporated and the dry residue was extracted with boiling ethyl acetate. Evaporation of the ethyl acetate solution yielded 0.76 g (58% of theory) of crystalline 2-oxopentane-1-sulfonamide of melting point 117° C.

EXAMPLE 8

Ethyl 2-amidosulfonyl-3-ketohexanoate

A mixture of 3.54 g (15 mmol) of ethyl 2-amidosulfonyl-3-aminohex-2-enoate and 42 ml of 4N HCl was stirred for 4 hours at 32°–34° C. After cooling to below 7° C., the crystals were filtered off with suction and washed with water until the washings were neutral (about 30 ml were required). The aqueous-acidic filtrate was concentrated in vacuo to a volume of about 20 ml to precipitate further crystals, which were filtered off with suction and washed with a small quantity of water. Drying of both the crystalline portions yielded 3.36 g (=94.4% of theory) of pure ethyl 2-amidosulfonyl-3-ketohexanoate of melting point 77°–78° C.

EXAMPLE 9

Ethyl 2-amidosulfonylacetoacetate

A mixture of 10.4 g of ethyl 2-amidosulfonyl-3-aminocrotonate and 65 ml of 4N HCl was kept for 1 hour at 30° C. and for 3 hours at room temperature and then concentrated in vacuo to a residual weight of 36 g. After standing for 17 hours at −40° C., the substrate which had crystallized out was filtered off with suction and rinsed with water. This yielded 6.6 g of pure ethyl 2-amido-sulfonylacetoacetate. The aqueous mother liquor was concentrated in vacuo to a residual weight of 15 g and then extracted with $CH_2Cl_2$. After drying, filtration and evaporation, the combined $CH_2Cl_2$ extracts left 3.5 g of a crystalline residue, which was recrystallized from ethyl acetate/diisopropyl ether (3:5) to yield 2.8 g of pure ethyl 2-amidosulfonylacetoacetate (melting point 65°–66° C.). The yield of ethyl 2-amidosulfonylacetoacetate was thus 9.4 g (=90%).

EXAMPLE 10

Methyl 2-amidosulfonylbenzoylacetate

A mixture of 2.57 g of methyl α-amidosulfonyl-β-aminocinnamate and 20 ml of 4N HCl was stirred for 2.5 hours at room temperature. The crystals were then filtered off with suction and rinsed with water. Drying yielded 2.40 g (=93%) of pure methyl 2-amidosulfonylbenzoylacetate of melting point 164°–165° C.

EXAMPLE 11

Ethyl-2-amidosulfonyl-3-amino-4-phenylcrotonate

A solution of 10.8 g (50.1 mmol) of ethyl 3-amino-4-phenylcrotonate in 40 ml of anhydrous acetonitrile was added dropwise, in about 15 minutes, at −5° C., to a solution of 3.10 g (26.8 mmol) of amidosulfonyl chloride in 20 ml of anhydrous acetonitrile. The mixture was stirred for 45 minutes at 0° C. to 2° C., for 45 minutes at 2° C. to room temperature and for 2 hours at room temperature, 4.8 ml of 6N NaOH were added dropwise at about 2° C. and the mixture was evaporated at a bath temperature of 38° C. to a residual weight of about 15 g. This residue was taken up in a mixture of 12 ml of water and about 100 ml of $CH_2Cl_2$, the phases were separated after thorough mixing and the aqueous phase was extracted a further 4× by shaking with $CH_2Cl_2$. The combined extracts were dried with $Na_2SO_4$ and filtered and the filtrate was evaporated in vacuo. The remaining residue (12.4 g) was chromatographed on a silica gel column (silica gel S; particle size 0.0063–0.2 mm; column $\phi$ 24 mm, h 520 mm; supplier Riedel de Haen). 1:1 $CH_2Cl_2$ petroleum ether was initially used as the eluent, with which excess ethyl 3-amino-4-phenylcrotonate or 3-amino-4-phenylacetoacetate was eluted. The proportion of $CH_2Cl_2$ in the eluent was continuously increased until, after a few intermediate fractions (1600 ml of eluate), the ethyl 2-amidosulfonyl-3-amino-4-phenylcrotonate was eluted with $CH_2Cl_2$. 4.74 g (=66.7%) of pure 2-amidosulfonyl ester were obtained as a viscous colorless oil (E/Z mixture):

$C_{12}H_{16}N_2O_4S$:

| | | | | |
|---|---|---|---|---|
| calc.: | C 50.7%; | H 5.7%; | N 9.9%; | S 11.3% |
| found: | C | H | N | S |

TLC ($CH_2Cl_2/EtOH$: 100/5): Rf 0.40.

2-Oxo-3-phenylpropane-1-sulfonamide 2.84 g (10 mmol) of ethyl 2-amidosulfonyl-3-amino-4-phenylcrotonate were dissolved in 15 ml of 2N sodium hydroxide solution at room temperature. After 16 hours, oily by-products were extracted with methylene chloride and the aqueous solution was adjusted to pH 1 with concentrated hydrochloric acid and heated for 15 minutes to 90° C. After evaporation of the aqueous solution, the residue was extracted with ethyl acetate and the extract was dried over sodium sulfate and evaporated again. This yielded 1.43 g (68% of theory) of crystalline 2-oxo-3-phenylpropane-1-sulfonamide.

EXAMPLE 12

Ethyl 2-amidosulfonyl-4-phenylacetoacetate 1.43 g (5 mmol) of ethyl 2-amidosulfonyl-3-amino-4-phenylcrotonate (according to Example 11) were treated with 45 ml of 4N HCl and stirred for 2.5 hours at 32–35° C. (the mixture remained in two phases during this time). Extraction was then carried out with ether. The dried ether extract was filtered and the filtrate was evaporated. This left 1.24 g of a crystalline residue, which was already virtually pure ethyl 2-amidosulfonyl-4-phenylacetoacetate. This substance was mixed with a small quantity of hexane and filtered off with suction. Drying yielded 1.16 g (=a yield of 81.3%) of pure ethyl 2-amidosulfonyl-4-phenylacetoacetate of melting point 77°–78° C.

What is claimed is:

1. A process for the preparation of 2-ketosulfonamide of the formula I

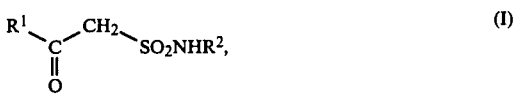

in which
$R^1$ is a $C_1$–$C_4$ alkyl radical, and
$R^2$ is a hydrogen atom,
wherein a 3-aminoalk-2-enoic acid ester of the formula II

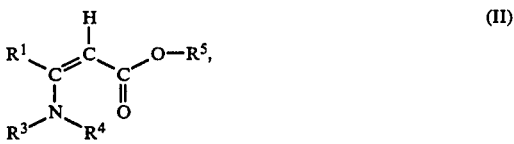

in which $R^1$ has the meaning given above, $R^3$ and $R^4$ are identical or different and are hydrogen, $C_1$–$C_4$ alkyl radicals which may be linked together to form a ring, or $C_6$–$C_{12}$ aralkyl or $C_6$–$C_{12}$ aryl radicals having 0 to 2 heteroatoms, and $R^5$ is a branched or unbranched $C_1$–$C_{18}$ alkyl radical which may contain heteroatoms, is reacted with an amidosulfonyl halide of the formula III

in which $R^2$ has the abovementioned meaning and X is chlorine, bromine or fluorine, in the presence of at least one equivalent, based on the ester used, of a base, and the resulting 3-amino-2-sulfamoylalk-2-enoic acid ester of the formula IV

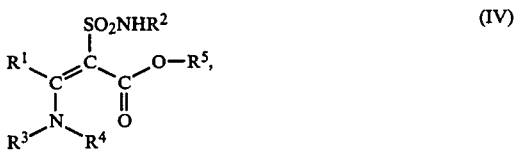

in which $R^1$, $R^2$, $R^3$, $R^4$ and $R^5$ have the abovementioned meanings, is subjected to acid or alkaline saponification and decarboxylation.

2. The process according to claim 1 in which the compound of the formula II is a 3-aminocrotonic acid ester having at least 1 hydrogen atom on the nitrogen atom.

3. The process according to claim 1 in which the compound of the formula IV is one in which $R^1$ is $C_1$–$C_4$ alkyl; $R^2$ is hydrogen; $R^3$ is hydrogen, methyl or phenyl; $R^4$ is hydrogen; and $R^5$ is $C_1$–$C_4$ alkyl.

4. A process for the preparation of 3-amino-2-sulfamoylalk-2-enoic acid esters of the formula IV

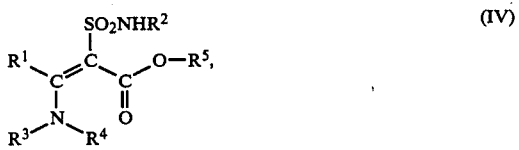

in which
$R^1$ is a $C_1$–$C_4$ alkyl radical, and
$R^2$ is a hydrogen atom, $R^3$ and $R^4$ are identical or different and are hydrogen, $C_1$–$C_4$ alkyl radicals which may be linked together to form a ring, or $C_6$–$C_{12}$ aralkyl or $C_6$–$C_{12}$ aryl radicals having 0 to 2 heteroatoms, and $R^5$ is a branched or unbranched $C_1$–$C_{18}$ alkyl radical which may contain heteroatoms, wherein a 3-aminoalk-2-enoic acid ester of the formula II

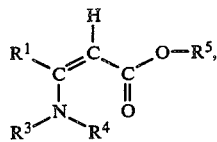
(II)

in which $R^1$, $R^3$, $R^4$ and $R^5$ have the abovementioned meanings, is reacted with an amidosulfonyl halide of the formula III

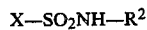 (III), in which $R^2$ has the abovementioned meaning and X is chlorine, bromine or fluorine, in the presence of at least one equivalent, based on the ester used, of a base.

* * * * *